United States Patent
Nogarin

(10) Patent No.: US 6,520,994 B2
(45) Date of Patent: Feb. 18, 2003

(54) SHOULDER ENDOPROSTHESIS FOR FRACTURES OF THE UPPER END OF THE HUMERUS

(75) Inventor: Livio Nogarin, Castel d'Azzano (IT)

(73) Assignee: Cremascoli Ortho S.A., Toulon Cedex (FR)

(*) Notice: Subject to any disclaimer, the term of this patent is extended or adjusted under 35 U.S.C. 154(b) by 0 days.

(21) Appl. No.: 09/764,080

(22) Filed: Jan. 19, 2001

(65) Prior Publication Data
US 2001/0011193 A1 Aug. 2, 2001

(30) Foreign Application Priority Data
Jan. 28, 2000 (IT) .................. MI2000A000122

(51) Int. Cl.[7] .................................................. A61F 2/40
(52) U.S. Cl. .................................................. 623/19.14
(58) Field of Search ........................... 623/19.11, 19.12, 623/19.13, 19.14, 23.15, 23.24, 23.25, 23.26, 23.28, 23.29, 23.31

(56) References Cited

U.S. PATENT DOCUMENTS

| | | | | |
|---|---|---|---|---|
| 4,608,053 A | * | 8/1986 | Keller | 623/23.31 |
| 4,944,763 A | * | 7/1990 | Willert et al. | 623/23.29 |
| 5,480,451 A | | 1/1996 | Moser et al. | |
| 5,489,309 A | * | 2/1996 | Lackey et al. | 623/19.14 |
| 5,728,161 A | | 3/1998 | Camino et al. | |
| 6,197,062 B1 | * | 3/2001 | Fenlin | 623/19.12 |
| 6,283,999 B1 | * | 9/2001 | Rockwood, Jr. | 623/19.12 |

FOREIGN PATENT DOCUMENTS

| | | |
|---|---|---|
| DE | 299 18 669 | 12/1999 |
| EP | 0 623 321 | 11/1994 |
| EP | 1 043 001 | 10/2000 |

\* cited by examiner

Primary Examiner—David J. Isabella
(74) Attorney, Agent, or Firm—Daniel O'Byrne

(57) ABSTRACT

A shoulder endoprosthesis for fractures of the upper end of the humerus, comprising a humeral stem, adapted to be accommodated in an intramedullary canal of the humerus and provided with multiple longitudinal ribs, and a humeral proximal part, which is suitable to couple to one end of the stem, is provided with a plurality of lateral fins and has, at an upper end, a portion for engagement with a humeral head which is suitable to reconstruct the head of the humerus of the patient.

7 Claims, 2 Drawing Sheets

SHOULDER ENDOPROSTHESIS FOR FRACTURES OF THE UPPER END OF THE HUMERUS

BACKGROUND OF THE INVENTION

The present invention relates to a shoulder endoprosthesis for fractures of the upper end of the humerus.

It is known that among the various kinds of fracture of the upper end of the humerus four-part fractures are the most severe and often require surgical treatment when the fragments of the fracture are mutually dislocated.

In a four-part fracture the muscles play a key role in the pathophysiology of this type of fracture, since they pull in different directions on each fragment of the fracture. As shown in FIG. 1, the diaphysis 1, the fragments of the inferior tuberosity 2, the upper tuberosity 3 and the humeral head 4 are separated one another and the fracture is not simple. Conservative treatment by surgical reduction is not satisfactory and very often causes pseudarthrosis or necrosis of the humeral head.

Accordingly, in these cases the only possible treatment that allows to recover complete mobility and eliminate pain is joint replacement.

Most surgical procedures that use shoulder joint prostheses are the consequence of fractures.

Currently known shoulder prostheses are mainly cemented and have holes in the proximal-lateral part in order to allow fixation of the tuberosities. However, the location of said holes makes it difficult to achieve stable fixation of the tuberosities; accordingly, fragment consolidation is often not achieved and patients complain of continuous pain and unsatisfactory mobility of the joint.

With most of the currently known shoulder prostheses, once the cement as set it is not possible to correct retroversion and therefore position the rosthesis appropriately.

SUMMARY OF THE INVENTION

The aim of the present invention is to provide a shoulder endoprosthesis which can be applied in the case of multiple fractures without requiring bone cement.

Within the scope of this aim, an object of the present invention is to provide a shoulder endoprosthesis which allows to restore humeral length and correct retroversion.

Another object of the present invention is to provide a shoulder endoprosthesis which allows to fix the tuberosities to the diaphysis as well as to the prosthesis.

Another object of the present invention is to provide a shoulder endoprosthesis which allows to reposition the tuberosities with the correct tension and in the correct seat.

Another object of the present invention is to provide a shoulder endoprosthesis which is highly reliable, relatively easy to manufacture and at competitive costs.

This aim and these and other objects which will become better apparent hereinafter are achieved by a shoulder endoprosthesis for fractures of the upper end of the humerus, characterized in that it comprises a humeral stem, which is suitable to be accommodated in an intramedullary canal of the humerus and is provided with multiple longitudinal ribs, and a humeral proximal part, which is suitable to couple to one end of said stem, is provided with multiple lateral fins and has, at an upper end, a portion for engagement with a humeral head which is suitable to reconstruct the head of the humerus of the patient.

BRIEF DESCRIPTION OF THE DRAWINGS

Further characteristics and advantages will become better apparent from the description of preferred but not exclusive embodiments of the shoulder endoprosthesis according to the present invention, illustrated only by way of non-limitative example in the accompanying drawings, wherein.

DESCRIPTION OF THE PREFERRED EMBODIMENTS

Figure 1:
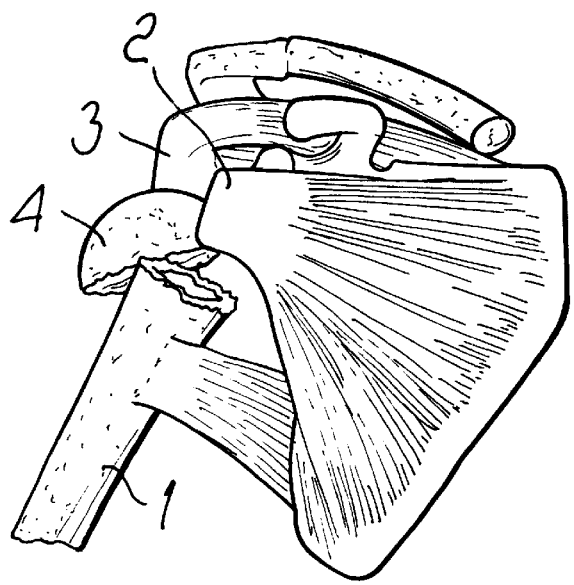
FIG. 1 is a perspective view of a four-part fracture of the upper end of the humerus.
Figure 2:
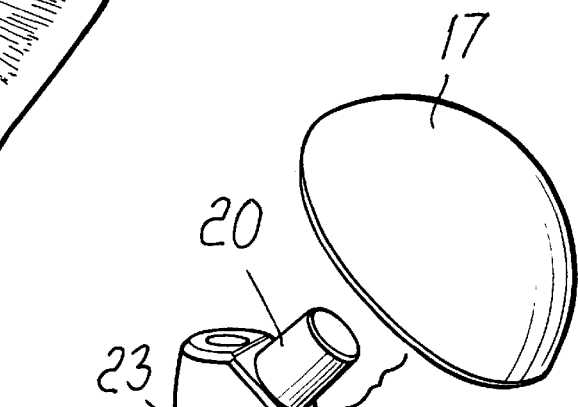
FIG. 2 is an exploded view of the shoulder endoprosthesis according to the present invention.
Figure 3:
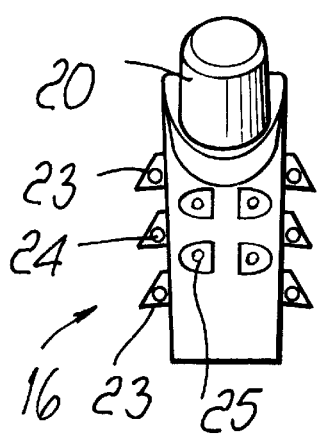
FIG. 3 is a front view of the humeral proximal part that constitutes one of the components of the endoprosthesis shown in FIG. 2.
Figure 4:
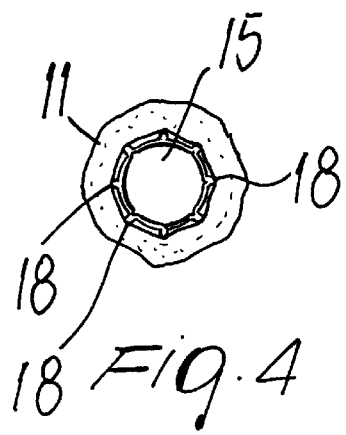
FIG. 4 is a plan view of the humeral stem, accommodated in the intramedullary canal of the humerus.
Figure 5:
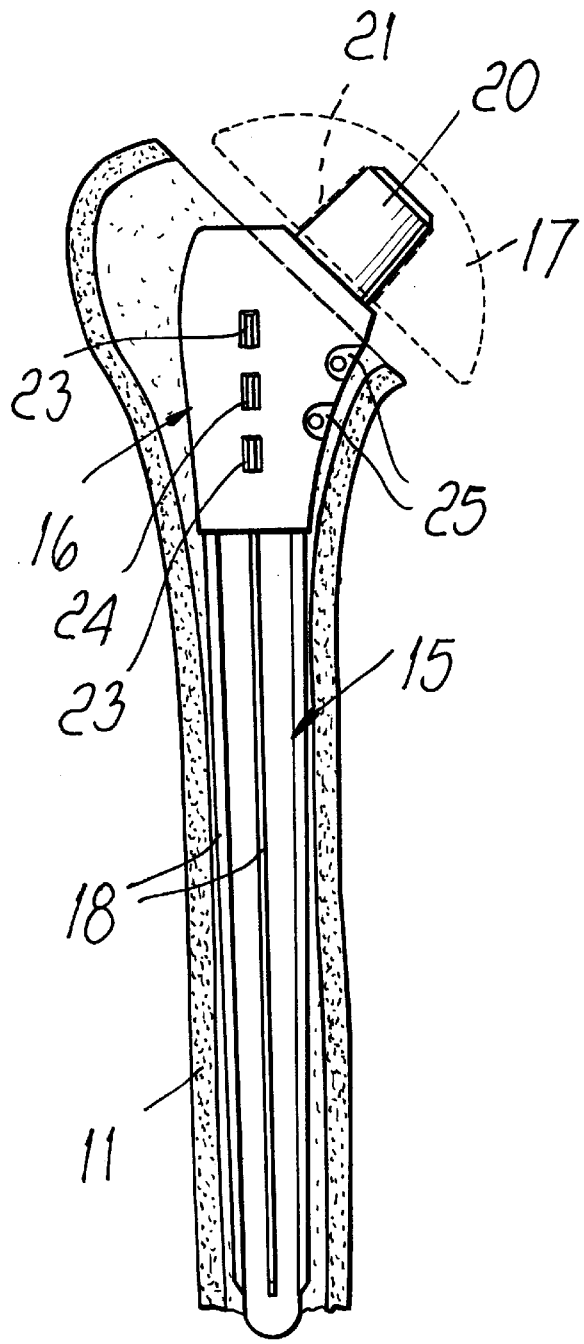
FIG. 5 is a schematic view of the insertion of the endoprosthesis according to the invention in the humerus.

With reference to the figures, and particularly to FIGS. 2 to 6, the endoprosthesis according to the present invention, generally designated by the reference numeral 10, comprises a humeral stem 15 designed to be inserted in the intramedullary canal of the humerus, which is designated by the reference numeral 11 in FIGS. 4 and 5.

The second component of the endoprosthesis according to the invention is constituted by the humeral proximal part 16, designed to couple to the humeral stem 15 at one end and to a humeral head 17 at the opposite end. The humeral head 17 constitutes the third component of the endoprosthesis and is conveniently constituted, for example, by a spherical portion.

In detail, the humeral stem 15 is a conical tubular element which has, on its lateral surface, longitudinal ribs 18 which are suitable to penetrate for a few tenths of a millimeter in the cortex of the humerus 11, ensuring excellent primary and secondary stability against rotation.

Conveniently, the humeral stem 15 is made for example of titanium alloy and tapers gently with a total angle of for example 2°.

FIG. 4 is a plan view of the insertion of the humeral stem 15 in the intramedullary canal of the humerus 11, with the longitudinal ribs 18 which engage the internal surface of the intramedullary canal of the humerus 11, allowing stable fixation of the humeral stem 15.

The second component of the endoprosthesis according to the invention, i.e., the humeral proximal portion 16, which is also for example made of titanium alloy, can be provided in different sizes, each having a different length.

The humeral proximal portion 16 is formed by a body which is shaped so as to engage, at one end, the conical end portion 19 of the humeral stem 15, and has, at the opposite end, a protruding conical portion 20 which is suitable to engage an appropriately provided seat 21 formed in the humeral head 17.

Conveniently, the conical portion 20 is angled with respect to the axis of the proximal part 16 and therefore of the stem 15.

Preferably, the angle of the conical portion 20 is approximately 135°.

The lateral surface of the proximal part 16 has a plurality of fins 23 which are suitable to allow fixation of the tuberosities in the bone in order to afford stable anchoring.

The fins 23 have holes 24 which allow to fix wires to the tuberosities.

Additional holes 25 for anchoring wires to the tuberosities are further provided in the anterior portion of the proximal part 16.

The holes 25 are through holes, as shown in the front view of FIG. 3.

The seat 21 formed in the humeral head 17 and suitable to allow the engagement of the conical portion or neck 20 can be conveniently provided with an axis which is inclined with respect to the axis of symmetry 32 of the humeral head 17.

In this case, the axis of the seat designated by the reference numeral 31 is substantially inclined with respect to the axis of symmetry 32. This allows better adaptation of the humeral head 17 to the anatomy of the proximal epiphysis.

Figure 6:
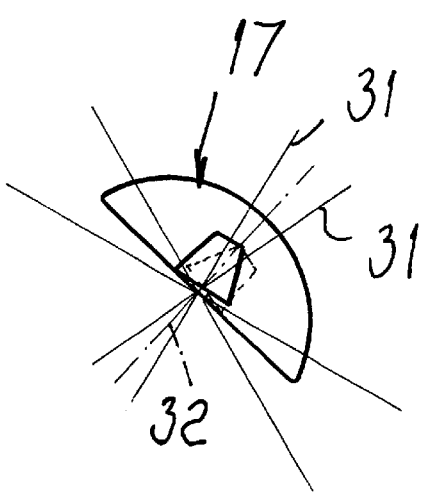
FIG. 6 is a view of a second embodiment of the humeral head which constitutes a component of the endoprosthesis according to the present invention.

FIG. 6 illustrates two different inclinations of the axis 31.

Essentially, the anchoring of the prosthesis according to the invention to the humerus is very simple, since it does not require the use of bone cement, and allows to fix the two tuberosities by using wires.

The humeral stem 15 is further inserted in the intramedullary canal of the humerus 11, also without using bone cement, and the longitudinal ribs 18 allow its stable anchoring.

In practice it has been observed that the shoulder endoprosthesis according to the invention fully achieves the intended aim, since it allows to reduce the fracture and restore joint function with a fully natural anchoring to the bone.

The endoprosthesis according to the invention is susceptible of numerous modifications and variations, all of which are within the scope of the inventive concept. All the details may furthermore be replaced with other technically equivalent elements.

In practice, the materials employed, so long as they are compatible with the specific use, as well as the dimensions, may be any according to requirements and to the state of the art.

The disclosures in Italian Patent Application No. MI2000A000122 from which this application claims priority are incorporated herein by reference.

What is claimed is:

1. A cementless shoulder endoprosthesis for fractures of the upper end of the humerus, comprising a humeral stem, which is configured to be accommodated in an intramedullary canal of the humerus, the stem being provided with a plurality of longitudinal ribs arranged circumferentially, and a humeral proximal part which is suitable to couple to one end of said stem, the proximal part being provided with a plurality of spikes protruding from anterior and posterior surfaces of the proximal part, the proximal part having, at an upper end, a portion for engagement with a humeral head which is suitable to reconstruct the head of the humerus of the patient, said ribs protruding from an outer surface of the stem and being adapted to penetrate through the cortical bone of the intramedullary canal of the humerus.

2. The endoprosthesis according to claim 1, wherein said humeral stem has a conical outer surface and said plurality of longitudinal ribs radially protruding from the outer conical surface of said stem.

3. The endoprosthesis according to claim 1, wherein said humeral proximal part has a medial surface region formed with a plurality of through holes.

4. The endoprosthesis according to claim 1, wherein each of said spikes has an aperture formed therein.

5. The endoprosthesis according to claim 1, wherein said portion for engagement of said humeral proximal part with said humeral head is frustum-shaped and angled with respect to an axis of said proximal part.

6. The endoprosthesis according to claim 5, wherein said humeral head has a substantially hemispherical surface having an undersurface formed with a centrally located recess for engagement with said portion for engagement of said humeral proximal part.

7. The endoprosthesis according to claim 6, wherein said centrally located recess has an axis which is substantially inclined with respect to the diametrical axis of said humeral head.

* * * * *